United States Patent [19]

Goldberger et al.

[11] Patent Number: 5,676,139
[45] Date of Patent: Oct. 14, 1997

[54] SPRING CLIP PROBE HOUSING

[75] Inventors: Daniel S. Goldberger, Boulder; Mark Hibl, Louisville; David R. Tobler, Westminster, all of Colo.

[73] Assignee: Ohmeda Inc., Liberty Corner, N.J.

[21] Appl. No.: 355,717

[22] Filed: Dec. 14, 1994

[51] Int. Cl.⁶ ........................................... A61B 5/00
[52] U.S. Cl. .............................. 128/633; 128/666; 356/41
[58] Field of Search ........................... 24/DIG. 11, 324; 128/633, 664–6, 630, 632, 736, 748, 639, 653.1, 691; 356/41

[56] References Cited

U.S. PATENT DOCUMENTS

| | | | |
|---|---|---|---|
| 1,840,604 | 1/1932 | Randall | 24/324 |
| 4,685,464 | 8/1987 | Goldberger et al. | |
| 5,217,012 | 6/1993 | Young et al. | 128/633 |
| 5,247,931 | 9/1993 | Norwood | 128/672 |
| 5,313,940 | 5/1994 | Fuse et al. | 128/633 |
| 5,437,275 | 8/1995 | Amundson et al. | 128/633 |
| 5,438,986 | 8/1995 | Disch et al. | 128/633 |

FOREIGN PATENT DOCUMENTS

| | | |
|---|---|---|
| 0 127 947 | 12/1984 | European Pat. Off. |
| 0 204 459 | 12/1986 | European Pat. Off. |
| 0 262 779 | 4/1988 | European Pat. Off. |
| 2 259 545 | 9/1991 | United Kingdom |

Primary Examiner—Robert Nasser
Attorney, Agent, or Firm—Roger M. Rathbun; William A. Schoneman; Salvatore P. Pace

[57] ABSTRACT

This probe makes use of a simplified housing construction that significantly reduces the cost of the manufacture of the probe housing. The housing is implemented using two molded housing halves, which are pivotally connected together and which include an integral spring member. In addition, the housing includes a connector mounted thereon for enabling the probe to be disengaged from the cable and its associated connector that interconnects the probe with the medical monitoring equipment. As a further improvement, a notch is provided on the housing so that the conductors can be positioned to exit the probe in any direction to minimize the possibility of the conductors inadvertently pulling the probe loose from the patient's finger.

21 Claims, 2 Drawing Sheets

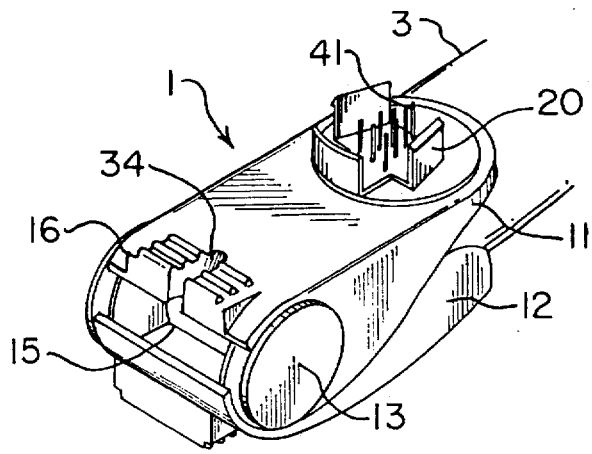
FIG. 1
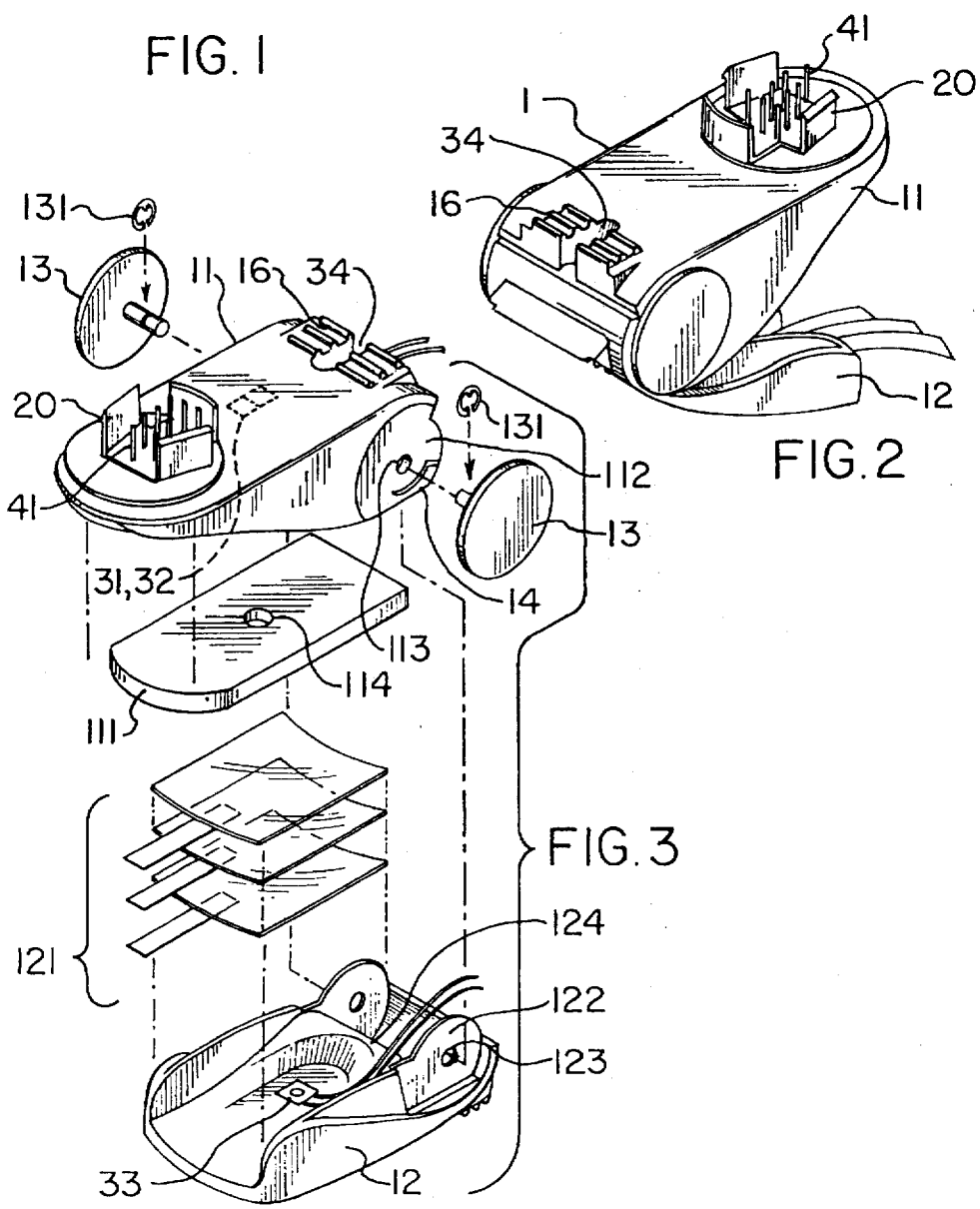
FIG. 2
FIG. 3

SPRING CLIP PROBE HOUSING

1. Field of the Invention

This invention relates to medical monitoring equipment, and in particular, to a spring clip probe housing that is used to attach the probe sensors, used to detect arterial blood flow, to a patient.

2. Background of the Invention

Medical monitoring equipment non-invasively monitors arterial blood flow to measure a number of patient characteristics, such as arterial pulse rate, oxygen saturation of the hemoglobin in the arterial blood, hemoglobin content of the arterial blood and other such characteristics of the blood. These measurements rely on the use of a probe that contains a plurality of light emitting diodes and at least one light detector. The probe is attached to the patient at a location that is rich in arterial blood. The light generated by the light emitting diodes is transmitted through the patient's tissue for detection by the light detector. The wavelengths of light generated by the light emitting diodes are selected such that the components in the arterial blood to be measured are either highly absorbing or minimally absorbing of that frequency of light. The amount of light transmitted through the patient's tissue is a measurement of the instantaneous quantity of blood that is present in the arterial system and the components contained in this arterial blood.

A significant difficulty with this type of sensor is that it is difficult to produce a probe housing that can be securely attached to a desired location on the patient, that precisely positions the light emitting diodes and the light detector, and yet is both simple to use and inexpensive to manufacture. Prior art probes include flexible material cut in a butterfly shape to conformably attach to the patient's finger, which flexible material is secured by means of an adhesive. A difficulty with this type of sensor housing is that the adhesive can fail, the flexible material can work loose from the patient's finger and the housing is not reusable.

An alternative probe consists of a clip type probe housing, illustrated in U.S. Pat. No. 4,685,464, which has two rigid arms hingeably connected in opposition and secured about a patient's finger. This clip type of probe housing includes a deformable pad in each arm thereof which receives, conforms to and securely grips the tissue of the patient's finger without significantly affecting arterial blood flow. The two arms of this probe housing are pivotally mounted and biased closed under tension by means of a spring. One of the pads contains a light source for illuminating the tissue while the other pad contains a light detector to measure the amount of light transmitted through the blood components. This probe housing however contains several undesirable features, one of which is a cost of manufacture and the number of components contained therein. In addition, the probe conductors are hard wired to the light emitting diode and the light detector and exit the probe housing from the end of the housing that points away from the patient. Therefore, any force applied to the conductors tends to pull the probe off the patient's finger. In order to minimize the possibility of this happening, medical personnel typically loop the conductors to be in alignment with the patient's arm and tape the conductors to the patient's arm. This loop itself applies tension to the probe, tending to forcing it out of alignment on the patient's finger and also provides an opportunity for the loop to snag any protruding object and pull the probe off the patient's finger. In addition, the probe and its conductors are a single integrated unit and cannot be reused from patient to patient. This increases the cost to use the medical monitoring equipment, since each use requires the disposal of the probe, its conductors and associated connector.

SOLUTION

The above described problems are solved and a technical advance achieved in the field by the spring clip probe housing of the present invention. This spring clip probe housing makes use of a simplified housing construction that significantly reduces the cost of manufacture of the probe housing. The spring clip probe housing is implemented using two molded housing sections, which are hingeably connected together and which include an integral spring member. The housing sections snap together via a pivot pin rather than requiring extensive labor to assemble. The housing sections, when placed in a closed position, encircle and securely affix the probe to a patient's finger to non-invasively measure characteristics of the arterial blood.

In addition, the probe housing includes a connector mounted thereon to enable the probe to be disengaged from the cable and its associated connector that interconnects the probe with the medical monitoring equipment. As a further improvement, this connector may be rotatably mounted on the housing so that the conductors' can be positioned to exit the probe in any direction to minimize the possibility of the conductors inadvertently pulling the probe loose from the patient's finger. Alternatively, an integral cable clip can be included in the exterior of the probe housing to securely position the cable in line with a patient's arm.

The interior surfaces of the two housing sections are curved to substantially parallel the contours of a patient's finger. One section includes a transparent material adhesively coated on both sides. The adhesive on one side of the material secures the material to the housing section while the adhesive on the other side functions to retain the patient's finger in a predetermined position within the probe housing when the two sections of the housing are in a closed position. The other section of the housing may include a conformable pad affixed to the interior thereof to assist in the retention of the patient's finger within the probe housing.

BRIEF DESCRIPTION OF THE DRAWING

FIG. 1 illustrates a perspective view of the spring clip probe housing in a closed position;

FIG. 2 illustrates a perspective view of the spring clip probe housing in an open position;

FIG. 3 illustrates an exploded view of the spring clip probe housing;

DETAILED DESCRIPTION

Figure 4:
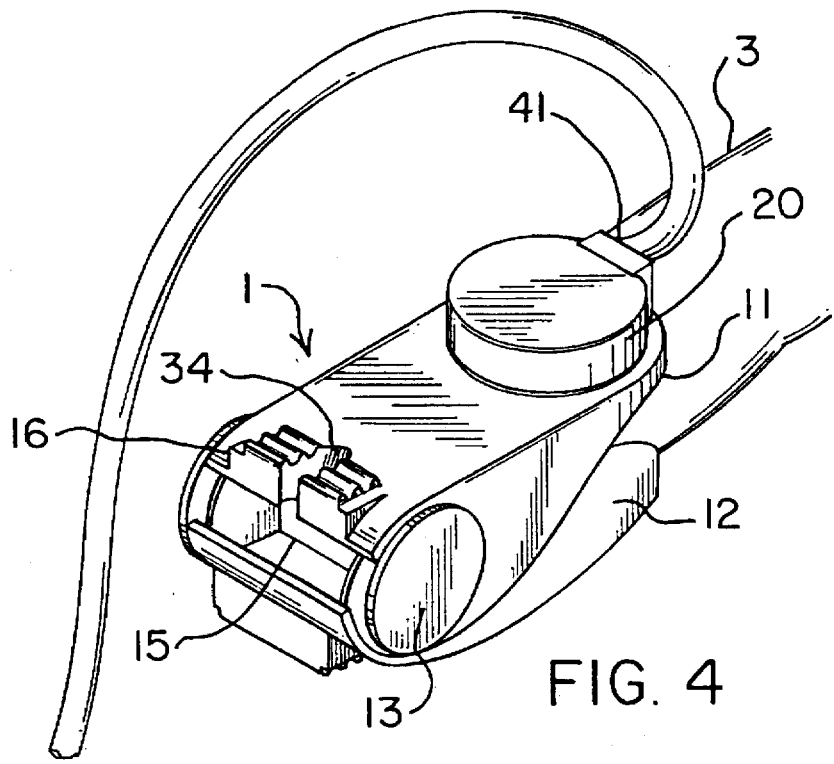
FIG. 4 illustrates additional details of the cable attachment to the spring clip probe housing.

FIGS. 1 and 2 illustrate a perspective view and FIG. 3 illustrates an exploded view of the spring clip probe housing 1 of the present invention. The spring clip probe housing 1 is used to affix the sensors 31–33 of a pulse oximeter system to a patient's member, such as a finger 3. A pulse oximeter instrument is a well known device used extensively in critical care areas or hospitals to monitor a subject's arterial percentage oxygen saturation ($SpO_2$) and pulse rate (PR). The pulse oximeter instrument performs these measurements by recording the absorption of light in perfused tissue at two or more wavelengths of light. The pulse oximeter instrument compares the time variant and time invariant portions of the light absorption signal at the two wavelengths of light and uses this data in a well known empirical relationship to compute both the pulse rate and arterial percentage oxygen saturation.

In order to perform the measurements on the subject, the pulse oximeter system includes a probe 1 which is releasably attached to a subject's finger 3 or other arterial rich member of the body. A typical configuration of sensor elements 31–33 includes first and second light emitting diodes 31, 32, each of which generates a beam of light centered about a predefined wavelength. The wavelengths of these two light sources differ and are selected to detect the desired characteristics of the arterial blood as is well known in the art. The two light emitting diodes 31, 32 are placed in the probe housing 1 in a manner to project the beams of light generated into the arterial tissue of finger 3 in order to illuminate this tissue. The probe housing 1 furthermore includes a light detector 33 which is positioned to measure the amount of light transmitted through the arterial tissue of finger 3 of the subject.

Housing Architecture

The spring clip probe housing 1 consists of a first section 11, which is equipped with a conformable pad 111 attached to the interior surface of first section 11. Also included in the first section 11 is a connector 20 for electrically interconnecting a cable 2 to the light emitting diodes 31,32 and light detector 33 included in the probe housing 1. The second section 12 of spring clip probe housing 1 includes light detector 33 and an adhesively coated material 121 that serves to affix the probe housing 1 to the patient's finger 3. The first section 11 and the second 12 section are similar in configuration and, when fitted together, function to press the light emitting diodes 31,32 and light detector 33 against a patient's finger 3 that is inserted between the first 11 and second 12 sections. The first 11 and second 12 sections are hingeably attached to each other and include a spring member 14 integral to the first section 11 that functions to bias the first 11 and second 12 sections together in a closed position as illustrated in FIG. 1. First 11 and second 12 sections include mating pieces that, when assembled with a pivot pin 13, function as a hinge. In particular, the first section 11 includes two areas 112, each of which has an aperture 113 formed therein to correspond to a mating aperture 123 in areas 122 on the second section 12. The first 11 and second 12 sections are aligned and interconnected by the insertion of pivot pins 13 in the respective apertures 113,123 when oriented opposite each other such that the tissue contacting surfaces of the interior surfaces of first and second sections 11,12 face each other. The integral spring 14 that is part of first section 11 exerts a force against the second section 12 to force the ends of the first and second housing sections 11,12 apart, which cause the first and second housing sections 11,12 to rotate with respect to each other around the pivot pins 13, thereby forcing the other ends of the housing together.

The interior surface of the first 11 and second 12 sections include a curved portion to substantially parallel the contours of a typical finger 3 to which the probe housing 1 is connected. The conformable pad 111, and adhesively coated material 121 function to compensate for topological differences between the patient's finger 3 and the curvature of the inside of the two sections 11,12 of the housing 1. Thus, when the two sections 11,12 of the probe housing 1 are closed about a patient's finger 3, the conformable pad 111 and adhesively coated material 121 form a surface that substantially maps to the contours of the patient's finger 3. The use of the conformable pad 111 and adhesively coated material 121 and the spring mechanism 14 of the probe housing 1 ensures that the light emitting diodes 31,32 and the light detector 33 are placed in close and firm contact with the skin of the patient's finger 3. The close contact of the light emitting diodes 31,32 and the light detectors 33 with the patient's finger 3 is critically important since any ambient light that is received by the light detector 33 interferes with the measurement of the particular characteristics of the arterial blood that are performed by the monitoring equipment.

The interior surface of the second section 12 is also shaped to match the contours of the bottom of a finger 3 such that the interior end 124 of this recess functions as a finger stop which is designed to position the patient's finger 3 inside of the housing section 12 at a predetermined location. The height of the finger stop 124 is designed to permit a fingernail, especially a long fingernail, to pass over the top, but also to prevent the fleshy fingertip from extending beyond a selected point between the two sections 11,12 of the probe housing 1. The light detector 33 is mounted in the bottom of the contoured area of second section 12 in a predetermined location and typically secured in place by a clear encapsulant.

Adhesive Pad and Adhesively Coated Material

Figure 5:
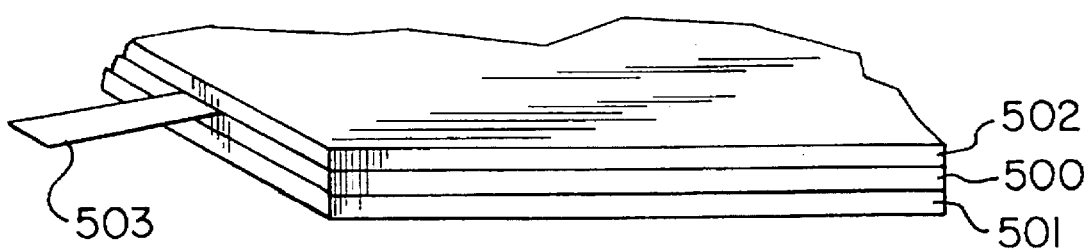
FIG. 5 illustrates additional details of the adhesive pad used in the spring clip probe housing.

In order to prevent the movement of the patient's finger 3 within the probe housing 1, the adhesively coated material 121 (also shown in FIG. 5) located in the second section 12 is implemented by means of at least one (shown in FIG. 5) and preferably a plurality (shown in FIG. 3) of layers of clear conformable material 500 that are adhesively coated on both sides thereof. The adhesive 501 on the bottom side of this material 500 retains adhesively coated material 121 in a predetermined position in the second section 12 of the housing 1 while the adhesive 502 on the top surface thereof functions to retain the patient's finger 3 in the predetermined position within the housing by means of a moderately secure adhesive force. Each of the layers of conformable material 500 can be provided with a pull tab 503 such that after a plurality of uses, when the adhesive 501,502 is reaching end of life, the user can withdraw that layer of conformable material 500 to expose the layer of conformable material beneath, providing an unused adhesive available for use with a subsequent patient.

Conformable material 500 and adhesive 501,502 is preferably made of a transparent material to enable the light beams transmitted by light emitting diodes 31,32 through finger 3 to pass unobstructed to light detector 33. The conformable pad 111 adhesively affixed to the first section 11 can be manufactured of an opaque material having an aperture (hole) 114 cut therein to allow the light emitting diodes 31,32 affixed to the interior surface of the first section 11 of the probe housing 1 to transmit their light through the hole 114 in the conformable pad 111 to shine on the patient's finger 3 at a predetermined location, such as near the cuticle of the finger.

The construction of the first section 11 and second section 12 of the probe housing 1 is such that, when closed on the patient's finger 3, the first 11 and second 12 sections have surfaces conforming to the patient's finger 3 and close akin to a clam shell. The hingeably connected ends of the first 11 and second 12 sections of the probe housing 1 are cut such that in a closed position an aperture 15 is provided between the first 11 and second 12 sections. This aperture 15 is closed when the first 11 and second 12 sections are opened to the full extent, the range of travel being determined by the size of the aperture 15. Therefore, when placed in a fully opened position the pivoting end of the first 11 and second 12 sections encounter each other, restricting the range of motion of the first 11 and second 12 sections.

Finger Grip Surface

The exterior surfaces of the first 11 and second 12 sections of the probe housing 1 are preferably formed to include finger grip surfaces 16 that function to provide a ribbed surface to enable the user to securely grip the probe housing 1 and apply force in a manner to cause the patient end of the probe housing 1 to open fully to accept the patient is finger 3. The use of the ribbed finger grip surfaces 16 provides an additional benefit of minimizing the size of the probe housing 1, since a large projection extending past the pivot point is unnecessary to provide a suitable gripping surface for the user.

Connector

The light emitting diodes 31,32 and the light detector 33 are of conventional design typically found in pulse oximeter probes. The plurality of conductors are connected to the light emitting diode 31,32 and light detector 33 devices and these conductors are terminated in a connector 20 located on the top surface of the first section 11 of the probe housing 1. This connector 20 includes a plurality of pins 41 arranged in a predetermined pattern therein, which connector 20 is located at the patient end of the probe housing 1 in order to provide the user with sufficient space to grasp the probe housing 1 for application to the patient's finger 3. The connector 20 located on the first section 11 of the probe housing 1 can optionally be rotatably affixed thereto to thereby enable the cable 2 and the mating connector piece 21 that is attached thereto to be oriented to face either the patient or the user. Alternatively, the connector 20 can be placed in a fixed relationship, as is illustrated in FIGS. 1 and 2, such that the cable 2 exits the mating connector piece 21 in a direction in line with the patient's arm and extending toward the patient. This simplifies the attachment of the cable 2 to the patient's arm to minimize the possibility of a cable pulling the probe housing 1 loose from the patient's finger 3. If the probe is to be used for a quick check of the patient's arterial blood characteristics and not affixed to the patient's finger 3 for an extended period of time, the cable 2, when oriented in the position illustrated in FIG. 4, can be looped and secured to the probe housing 1 via a notch 34 formed into the middle of the finger grip surfaces 16 on the top of the first section 11 of the probe housing 1. This enables the user to secure the cable 2 in place with a small loop, thereby removing the tension placed on the probe housing 1 by the cable 2.

Alternative Embodiments

There are numerous alternative configurations of this apparatus, such as supplementing the adhesively coated material 121 with another conformable pad of the type (111) used in the first section 11. The shape and size of the probe housing 1 can be adapted to fit adult patients or infants or even constituted to attach to other body parts to perform the same function. While the probe housing 1 is shown constructed with two pivot pins 13 inserted through the openings in the first 11 and second 12 housing and secured in place by a C-spring 131, it is obvious that many other methods of fastening can be used herein, such as snap fit pivot pins that extend from one edge of the first section 11 to the other edge thereof or snap fit pivot pins that extend through the aperture 113,123 in the first 11 and second 12 sections of the housing 1 wherein one snap fit pivot pin is used on either side thereof.

It is to be expressly understood that the claimed invention is not to be limited to the description of the preferred embodiment but encompasses other modifications and alterations within the scope and spirit of the inventive concept.

We claim:

1. A probe for releasably attaching to a member of a patient under test, comprising:

a first housing section;

a second housing section hingeably attached to said first housing section to form a clamshell-type housing, said first and said second sections being rotatable between an open and a closed position and having an aperture in one end thereof when in said closed position to receive a member of a patient, with said first and said second housing sections both having an interior surface facing each other and an exterior surface;

means attached to said interior surface of said first housing section for transmitting a signal through said member;

means attached to said interior surface of said second housing section for receiving said transmitted signal which passes through said member: and, adhesive sheet means attached to said interior surface of said second housing section for attaching said second housing section to said member when said first and said second sections are in said closed position to place said adhesive sheet means in contact with said member positioned between said first and said second housing sections;

wherein said adhesive sheet means is a transparent sheet of material for providing an unobstructed path for said transmitted signal from said member to said receiving means.

2. The probe of claim 1 further comprising:

deformable means attached to said interior surface of said first housing section for compliantly conforming to said member when said first and said second housing members are in said closed position to place said deformable means in contact with said member.

3. The probe of claim 2 wherein said deformable means includes an aperture for providing an unobstructed path for said signal between said transmitting means and said member.

4. The probe of claim 1 wherein said adhesive sheet means comprises at least one sheet of transparent material having adhesive on opposite surfaces thereof, the adhesive of a first of said opposite surfaces functioning to attach said adhesive sheet means to said interior surface of said second housing section.

5. The probe of claim 4 wherein said adhesive on a second of said opposite surfaces functions to adhesively attach said adhesive sheet means to said member when said first and said second sections are in said closed position to place said adhesive sheet means in contact with said member positioned between said first and said second housing sections.

6. The probe of claim 5 wherein said adhesive sheet means further comprises:

tab means graspable by a user to enable a user to remove said adhesive sheet means from said interior surface of said second housing section by pulling on said tab means.

7. The probe of claim 1 wherein said adhesive sheet means comprises a plurality of sheets of transparent material stacked one on top of the other, each of said sheets of transparent material having adhesive on opposite surfaces thereof, the adhesive of a first of said opposite surfaces functioning to attach each said adhesive sheet means to a successive said adhesive sheet means in said stack and the bottommost said sheet of transparent material in said stack to said interior surface of said second housing section.

8. The probe of claim 7 wherein said adhesive on a second of said opposite surfaces functioning to adhesively attach each said adhesive sheet means to a successive said adhesive sheet means in said stack and the topmost said sheet of transparent material in said stack to said member when said first and said second sections are in said closed position to place said adhesive sheet means in contact with said member positioned between said first and said second housing sections.

9. The probe of claim 1 further comprising:
   at least one sensor element attached to said interior surface of at least one of said first and said second housing sections; and
   connector means attached to said exterior surface of said first housing section and connected to said at least one sensor element via a plurality of conductors for releasably interconnecting said probe with a cable.

10. The probe of claim 9 wherein said first housing section includes:
    notch means for securing said cable to said first housing section.

11. The probe of claim 1 wherein said second housing section includes a depression in said interior surface of said second housing section and of topology to substantially match the contours of said member.

12. The probe of claim 11 wherein said second housing section includes a projection in said interior surface of said second housing section at the end of said depression proximate to said hingeable connection of said first housing section and said second housing section for precisely positioning said member in said housing.

13. The probe of claim 1 further comprising:
    spring means for biasing said first and said second housing sections in their closed position.

14. A probe for releasably attaching to a member of a patient under test to illuminate said patient's tissue to measure predefined blood components of said member, comprising:
    a first housing section;
    a second housing section hingeably attached to said first housing section to form a clamshell-type housing, said first and said second sections being rotatable between an open and a closed position, with said first and said second housing sections both having an interior surface facing each other and an exterior surface;
    spring means for biasing said first and said second housing sections in their closed position;
    deformable means attached to said interior surface of said first housing section for compliantly conforming to said member when said first and said second housing members are in said closed position to place said deformable means in contact with said member;
    adhesive sheet means attached to said interior surface of said second housing section for attaching said second housing section to a member when said first and said second sections are in said closed position to place said adhesive sheet means in contact with said member positioned between said first and said second housing sections;
    means attached to said interior surface of said first housing section for transmitting a signal through said member;
    means attached to said interior surface of said second housing section for receiving said transmitted signal which passes through said member;
    connector means attached to said exterior surface of said first housing section and connected to said receiving means and said transmitting means via a plurality of conductors for releasably connecting said probe to a cable; and,
    wherein said adhesive sheet means comprises at least one sheet of transparent material having adhesive on opposite surfaces thereof the adhesive of a first of said opposite surfaces functioning to attach said adhesive sheet means to said interior surface of said second housing section.

15. The probe of claim 14 wherein said adhesive on a second of said opposite surfaces functioning to adhesively attach said adhesive sheet means to said member when said first and said second sections are in said closed position to place said adhesive sheet means in contact with said member positioned between said first and said second housing sections.

16. The probe of claim 15 wherein said adhesive sheet means further comprises:
    tab means graspable by a user to enable a user to remove said adhesive sheet means from said interior surface of said second housing section by pulling on said tab means.

17. The probe of claim 14 wherein said adhesive sheet means comprises a plurality of sheets of transparent material stacked one on top of the other, each of said sheets of transparent material having adhesive on opposite surfaces thereof, the adhesive of a first of said opposite surfaces functioning to attach each said adhesive sheet means to a successive said adhesive sheet means in said stack and the bottommost said sheet of transparent material in said stack to said interior surface of said second housing section.

18. The probe of claim 17 wherein said adhesive on a second of said opposite surfaces functioning to adhesively attach each said adhesive sheet means to a successive said adhesive sheet means in said stack and the topmost said sheet of transparent material in said stack to said member when said first and said second sections are in said closed position to place said adhesive sheet means in contact with said member positioned between said first and said second housing sections.

19. The probe of claim 14 wherein said first housing section includes:
    notch means for securing said cable to said first housing section.

20. The probe of claim 14 wherein said second housing section includes a depression in said interior surface of said second housing section and of topology to substantially match the contours of said member.

21. The probe of claim 14 wherein said second housing section includes a projection in said interior surface of said second housing section at the end of said depression proximate to said hingeable attachment of said first housing section to said second housing section for precisely positioning said member in said housing.

* * * * *